United States Patent [19]
Ernst et al.

[11] 3,961,627
[45] June 8, 1976

[54] AUTOMATIC REGULATION OF RESPIRATORS

[75] Inventors: Heini Ernst, Witterswil; Albert Guenin, Therwil, both of Switzerland

[73] Assignee: Hoffmann-La Roche Inc., Nutley, N.J.

[22] Filed: Sept. 3, 1974

[21] Appl. No.: 502,846

[30] Foreign Application Priority Data
Sept. 7, 1973   Switzerland.................... 12896/73

[52] U.S. Cl. .................... 128/145.8; 128/DIG. 29
[51] Int. Cl.² .................................... A61M 16/00
[58] Field of Search .......... 128/145.8, 145.5, 145.6, 128/142, 142.2, 142.3, 188, 145 R

[56] References Cited
UNITED STATES PATENTS

| | | | |
|---|---|---|---|
| 3,033,195 | 5/1962 | Gilroy et al. | 128/145.8 |
| 3,756,229 | 9/1973 | Ollivier | 128/145.8 |
| 3,794,059 | 2/1974 | Burt, Jr. | 128/142.2 |
| 3,831,596 | 8/1974 | Cavallo | 128/145.8 |

*Primary Examiner*—Robert W. Michell
*Assistant Examiner*—Henry J. Recla
*Attorney, Agent, or Firm*—Samuel L. Welt; George M. Gould; Mark L. Hopkins

[57] ABSTRACT

Regulation of the flow and pressure of the respiration gas in a respirator coupled to a patient is disclosed in regard to a respirator arrangement having a flow and pressure measuring device arranged proximate the patient connection for determining the flow and pressure of the respiration gas and converting the magnitudes, measured into electrical signals and also valve means arranged between the respiration gas source and the measuring device for controlling the flow and pressure of the respiration gas. Means are provided for obtaining a control signal for modulating the valve means by comparing the actual values measured for the flow and pressure with nominal values which themselves are calculated from preselected fixed values and said actual values.

24 Claims, 8 Drawing Figures

AUTOMATIC REGULATION OF RESPIRATORS

BACKGROUND OF THE INVENTION

This invention relates to regulation of the flow and pressure of the respiration gas in a respirator, and concerns a flow and pressure measuring device (arranged in the immediate vicinity of the patient connection) for determining the flow and pressure of the respiratory gas and converting the magnitudes measured into electrical signals, as well as a valve arrangement (arranged between the respiration gas source and the measuring device) for controlling the flow and pressure of the respiration gas. Further, the invention concerns as electronic regulator for carrying out this regulation.

The common respirators are controlled systems, i.e. their functional sequence is governed by rigidly specified input magnitudes. A group of known respirators includes the so-called pressure-controlled systems, with which respiratory gas is delivered under pressure to the patient, wherein a control valve interrupts the delivery of the respiratory gas if a certain specified pressure is built up in the line leading to the patient.

A further group includes the so-called volume-controlled systems, by which an amount of the respiration gas measured according to volume is delivered to the patient. Both types of respirators have at least the one disadvantage, which is principally inherent to all controlled systems, that they cannot react to compensate for changes in the lung mechanics not detectable in advance.

There have also previously been suggested automatically controlled respirators which, however, are not suitable for a wide routine employment in hospitals for various reasons. One such reason, for example, is that the measurement of the regulatory magnitude, there are necessary complicated devices which in addition are on the one hand expensive and on the other hand susceptible to disorders.

With respect to this problem, hitherto the possibilities of offering an automatic regulation have, to the disadvantage of the patient, not been pursued.

Summary of the Invention

The present invention is based on the task of utilizing the possibilities which lie in the automatic regulation of a respirator, i.e. to make available a regulatory process and a regulator, which combines, on the one hand, flexibility with respect to choice of program and compensation of disorders of magnitude measured therewith, and on the other hand, safe observation of limiting values specified by the doctor.

This is achieved in accordance with the invention by a regulation of the above-mentioned type, which is distinguished in that a control signal for modulating the valve is obtained by comparison of the actual values measured for flow and pressure with nominal values which are calculated from fixed values and the actual values.

Accordingly, a device suitable for carrying out this regulation contains an electronic circuit for calculating nominal values for pressure and flow from the actual values measured and given values, circuits for comparing the nominal values with the actual values, and a control circuit for controlling the valve.

The previously mentioned flexibility, which the regulation should have in accordance with the invention, is to be ensured not only with respect to the control of the respirator by the doctor or the attendant replacing him but also with respect to the accommodation of the individual and instantaneous requirements on the part of the patient. It has been provided to make optional the following values determining the course of the single respiration cycle:

1. Pressure increase during inspiration $(dP/dt)_I$

The magnitude of the pressure increase is set, above all, at the upper end by the pain sensations of the patient, which sensations with certain injuries, e.g. with rib fractures etc., can be increased. The lower limit of this magnitude is produced by the requirement to deliver a sufficient amount of respiration gas to the patient within the inspiration.

2. Pressure decrease during expiration $(dP/dt)_E$

The expiratory pressure decrease has to proceed as smoothly as possible in certain types of illness, e.g. emphysema. Normally, however, it is made steep, that is often the pressure becomes negative in the sense of an expiratory respiration assistance.

3. Final expiratory pressure $P_{E\ fin}$

This pressure is to be optional, because there is still no agreement in medicine on its optimal value and, as a result of this, to some extent not only atmospheric pressure but also positive and negative pressures are chosen.

4. Pressure in the expiratory inflexion $P_I$

This pressure value usually has no direct physiological significance. The necessity to be able to choose it results from the fact that $(dP/dt)_E$ and $P_{E\ fin}$ are made optional. If the gradient of the pressure decrease is specified, there must be determined namely a pressure value from which the final expiratory pressure is attained on a curve which is principally optional but usually linear.

5. Respiration frequency

It must be optional in a relatively wide range, since the regulation is to be used not only for adults but also for children, infants and babies.

6. Ratio of inspiration to expiration.

Apart from these magnitudes which are chosen for the single respiration cycle, there must also be provided a selectivity of respiration gas volume which is to be delivered to be patient. In principal, this nominal volume could also be specified per inspiration. It would be preferable, however, to specify the volume delivered during a time unit encompassing several respiration cycles, i.e. the respiration minute volume. From this and the respiration frequency, there is calculated the nominal volume per cycle. Moreover, the possibility would be provided to adjust the pulmonary alveolar minute volume and the dead volume separately, instead of the buccal minute volume.

Moreover, the possibility is given, as is evident in detail from the following description of an embodiment of the invention, to choose four different operational methods of regulation.

1. Controlled Respiration

The regulation pursues a respiration according to values fixed by the doctor. The apparatus allows for variations in the elastic resistance of the lungs (compliance) of the patient. The respiration is momentarily interrupted when the patient coughs.

2. Assisted Respiration

As long as the patient is unconscious, the respirator is regulated as in the controlled method of operation. When the patient is conscious, the regulation allows to a certain extent variations in the respiration frequency. The patient is permitted to increase his minute volume, either by increasing the volume per inspiration or the respiration frequency. The patient can also interpose a sigh or a short respiration pause. In contrast, a reduction in the respiration minute volume with respect to the fixed value is not allowed by the regulation. By suitable adjustment of the control elements, as is evident from the more precise description in the following, the intensity of the respiration assistance can be adjusted.

3. Spontaneous Respiration

With this method of operation, the patient is completely free in his respiration. The respirator provides for a constant buccal pressure independent of flow. Since in this method of operation, the respiration minute volume is not guaranteed, the regulator acts as a respiration minute volume monitor.

4. Manual Respiration

This possibility is normally only briefly used by the doctor during a surgical operation, i.e. as a brief interuption of the controlled respiration. In so doing, the whole regulator is inoperative. The doctor can manually control the respiration gas in both directions via the control valve. In case of a current interuption, this method of operation can serve for the short term.

DESCRIPTION OF THE PREFERRED EMBODIMENT(S)

Figure 1:
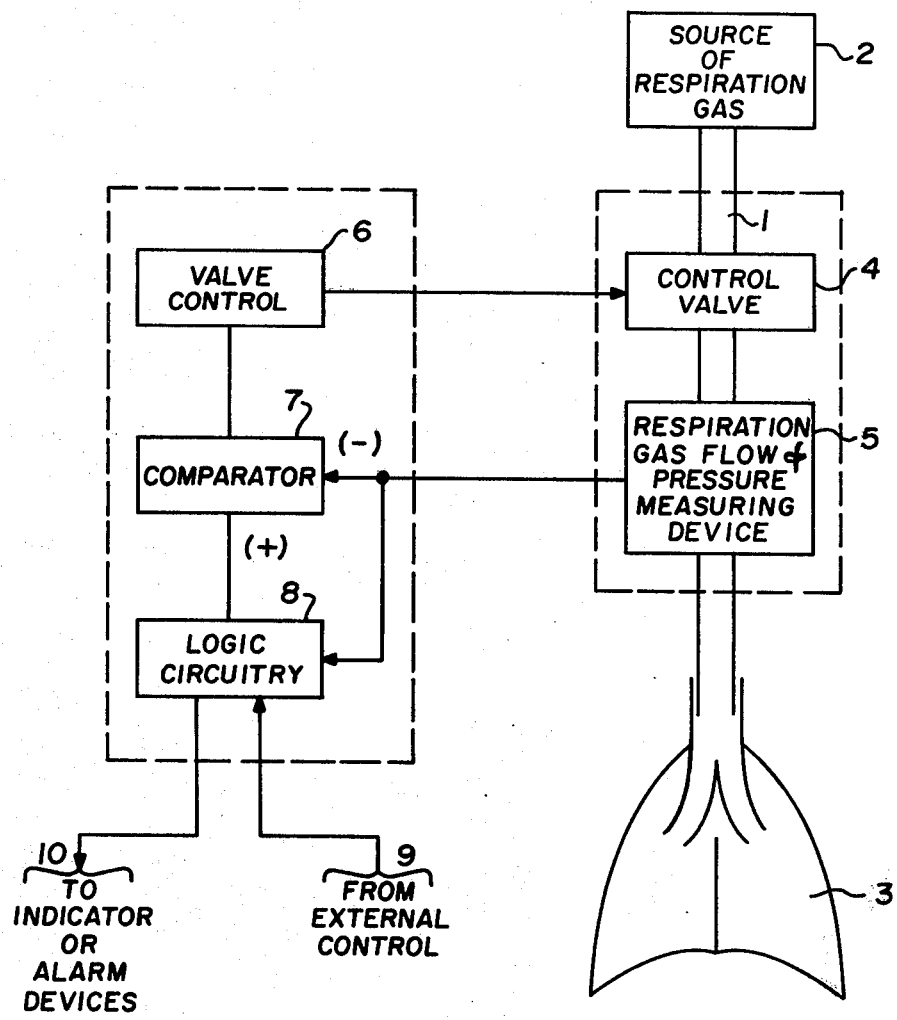
FIG. 1 shows in block diagram form a respirator in accordance with the invention.

A respirator which contains a regulator in accordance with the invention is divided into two sections as indicated in FIG. 1 by dotted lines. The first section, which represents the regulation system according to regulation technology includes the respiration gas line 1 from the respiration gas source 2 to the patient 3. In the immediate vicinity of the patient connection, there are arranged in the respiration gas line a control valve 4 and a measuring device 5 for measuring the flow and pressure of the respiration gas. The driving mechanism of the valve 4, for example, a servomotor, receives its control signal from a valve control 6 which is arranged in a section separated from the first section. The valve control 6 itself receives a control signal from a comparator circuit 7, in which the nominal and actual values for the flow and pressure of the respiration gas are compared with one another. The actual values are delivered to this circuit in the form of electrical signals, which the measuring device derives from the flow and pressure values measured. The nominal values come from a logic circuit 8, to which the actual values are likewise delivered. The logic circuit 8 has, apart from the input for the actual values, a series of inputs which are symbolized by the arrow 9 and come from the external control elements. The logic circuit 8 also has a series of outputs which are symbolized by the arrow 10 and which lead to indicator units or alarm devices. The comparator circuit 7 and the logic circuit 8 together represent a regulator in the sense of the present invention. It is to be observed that the comparator circuit 7 represented in simplification in FIG. 1, in reality consists of two comparator circuits since the flow and pressure of the respiration gas are regulated separetely.

On the basis of this greatly simplified scheme of an automatically regulated respirator, there is now firstly described the regulation in the controlled and the assisted method of operation, while the detailed description of the regulator follows subsequently. In the controlled respiration, the flow and pressure of the respiration gas are continuously measured at the month of the patient. The inspiration and the expiration is determined by the flow direction of the air. Both together form a respiration cycle.

Figure 2:
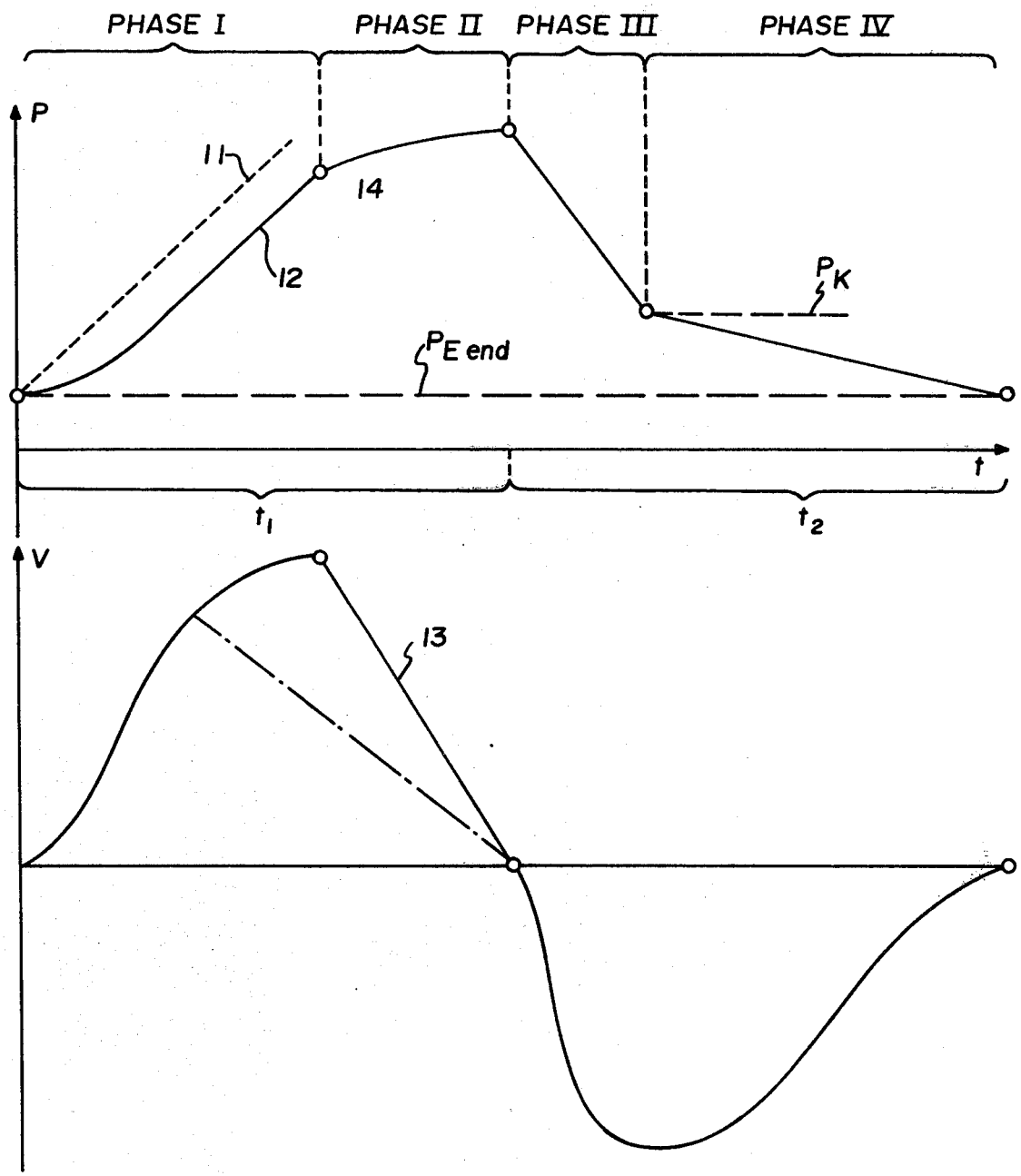
FIG. 2 graphically illustrates a four-phase control cycle comprising the cyclic course of nominal values for the flow and pressure as calculated by the logic circuitry of FIG. 1 based on actual values measured for the flow and pressure as well as values fixed by the attenting physician.

From the actual values measured for the flow and pressure as well as from the values fixed by the doctor, the logic circuit 8 calculates the nominal values for the flow and pressure. The cyclic course of these nominal values is defined as a control cycle. This control cycle consists of four phases, the phases I, III and IV being pressure-regulated and the phase II being flow-regulated and is illustrated in FIG. 2.

The respiration cycle and the control cycle do not necessarily have to fall together in time: mostly however, the phases I and II of the control cycle correspond to the inspiration and the phases III and IV of the control cycle correspond to the expiration.

The control cycle time (sum of the time of the phases I to IV) is calculated from the fixed frequency and the time of the phases I and II as well as the time of the phases III and IV is calculated from the fixed respiration time ratio (inspiration/expiration).

As mentioned, the phase I is pressure-regulated. By way of the final expiratory pressure $P_{E\ fin}$ measured with the measuring device 5, a linearly increasing pressure signal is calculated in the logic circuit 8 according to the $dP/dt$ fixed by the doctor. In order to bring about a smooth onset of inspiration, the pressure ramp is slightly delayed. The time constant of the delay amounts to 1/10 to 1/5 of the inspiration time. In FIG. 2, the fixed pressure increase $dP/dt$ is indicated by the line 11 and the delayed pressure curve by the curve 12.

From the measured flow V, the instantaneously inspired air volume $V_x$ is continuously calculated and compared with the inspiratory nominal volume $V_{nom}$. From this, the continuously decreasing residual volume $(V_{nom} - V_{act})$ is produced. A further volume is continuously calculated from the instantaneous flow measured at the mouth and a flow decreasing linearly to 0 from that point to the end of phase II. A linear flow curve 13 is in the present case only based on reasons of simplicity. In principal, any other flow curve, for example an exponential etc., could obviously be brought into this calculation. When the latter volume is identical with the residual volume, i.e. when $$\tfrac{1}{2} \dot{V} (t_1 - t_x) = V_{nom} - V_x$$

phase II begins. At this point 14, a transition from the pressure-regulated phase I to the flow-regulated phase II is possible without discontinuity in the flow and pressure progress. By this means, the inspiratory nominal volume is normally attained at the end of phase II.

Figure 3:
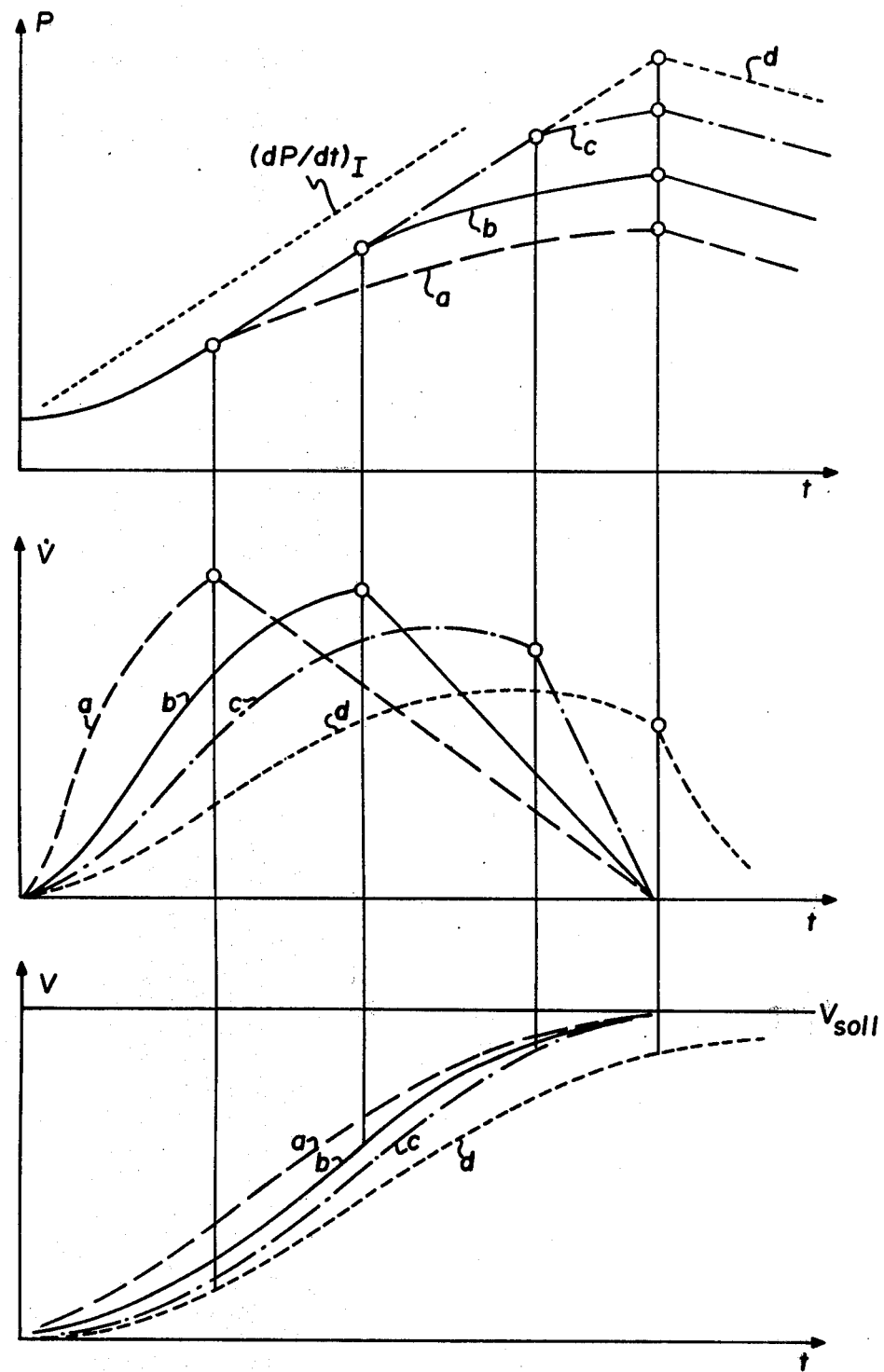
FIG. 3 shows different forms of the pressure, flow and volume curves during the inspiration phase.

As the various curves a to d in FIG. 3 show, the duration of phase I is greatly dependent on the elastic resistance of the lungs (compliance). To indicate the ratio of the duration of phase I with respect to phase II, which has a certain physiological significance, there can be used, for example, a series of lamps.

The two expiration phases III and IV are in turn pressure-regulated. The doctor can choose the pressure course with the three control elements for the expiratory pressure decrease, the inflexion and the final expiratory pressure. In phase III, the pressure proceeds from the pressure measured at the end of phase II according to a fixed pressure decrease $dP/dt$. When the pressure measured in phase III reaches the inflexion, the pressure proceeds linearly to the fixed final expiratory pressure. The part of the expiration from the inflexion to the end of the respiration cycle represents phase IV. The linear course of the pressure in the expiration represents a preferred embodiment, but could be replaced by another course of the pressure curve, for example, an exponential.

In order to avoid incorrect adjustments, the logic circuit takes care that phase IV is never shorter than phase III, i.e. the logic switches to phase IV at the latest after completion of the half expiration time. An incorrect adjustment would have as a result, for example, the onset of inspiration at an incorrect point in time or the occurrence of the so-called "air-trapping", i.e. too little expiration.

For the switching from pressure to flow control taking place during inspiration, it is important that no discontinuity results in the flow and pressure curve. Moreover, the condition exists that the inspiratory nominal volume calculated beforehand is attained at the end of phase II.

The inspiratory nominal volume is calculated on the one hand from the fixed values of respiration frequency and minute volume or alveolar minute volume and dead volume and on the other hand a correction value derived from the expiration. This correction value is the expired air volume per respiration cycle averaged over several respiration cycles (in the present embodiment six). Its calculation is effected such that during six respiration cycles, the expired air volume per respiration cycle is recorded and an average value is then formed. In this manner, the nominal value remains constant in each case for six respiration cycles. Deviations determined lead to a new nominal value for the next six respiration cycles.

In this manner, the danger of "air-trapping" is greatly reduced. Small leaks in the respiration system are automatically compensated. If a large correction (e.g. more than 20%) is necessary, an alarm is triggered. This alarm limit is only fixed at +20%. A negative correction is not limited and does not cause an alarm since it can occur at normal ratios in the assisted respiration to be described in the following.

The correction logic, in contrast, no effect on the subsequent six respiration cycles with a cough disturbance, when using the "manual" control and with a change in the nominal value adjustments of the control elements for frequency, minute volume and dead volume. In all of these cases, the logic behaves, with the aid of a stoppage, as in the case of a new start-up of the apparaatus, i.e. for the next six respiration cycles it yields inspiratory nominal volumes calculated according to the instantaneous adjustment without consideration of the measurement of the expiration air.

It is conceivable that phase II or the automatic switching to flow control cannot take place, if the pressure increase for the inspiration has been made too small, the compliance of the patient fluctuates greatly or the tube of the patient is congested. In these cases, the continuously calculated residual volume is constantly too large. In such a case, at the end of the time calculated for the phases I + II, phase I is switched directly to phase III. The respiration is then completely pressure-controlled. Indeed, the inspiratory nominal volume is not attained at the instant of beginning of phase II, but because of the lack of flow control, there results mostly (depending on the fixed $dP/dt$) an automatic extension of the inspiration period with respect to the expiration. With this, the chance is increased of nevertheless attaining the inspiratory nominal volume. A visual display indicates this anomalous course (disappearance of phase II). If this situation only occurs in a single respiration cycle, then the volume deficiency resulting from this is automatically taken into account in the next six respiration cycles. If, however, the situation occurs in several respiration cycles, then the feedback can no longer compensate for this large volume deficiency (more than 20%) and an alarm is triggered.

The present circuit offers the possibility of determining the cause of the alarm triggering. If the nominal correction is greater than 20% and phase II still comes into action, then this signifies that the fixed nominal value has probably been attained in inspiration but the expiratory volume measurement displays a smaller volume value. This signifies that a leak is present in the system. If the nominal correction is greater than 20% and phase II does not commence, then the apparatus is not capable of producing the fixed nominal volume in inspiration, be it because of congestion in the respiration path or too low an inspiration pressure. In this case, it is a question of an incorrect adjustment of the pressure increase for the patient in question or the necessity to carry out a cleansing of the mouth.

In the assisted respiration, the basic principle of the regulation remains the same as in the controlled respiration. Care is taken, however, that the patient is ensured a maximum of freedom with respect to respiration, the fixed minute volume representing the minimal value with which the patient respires. The patient can receive a larger volume, that is either by sighs, by a continuous increase of the inspiratory volume or an increase of the respiration frequency. It is possible, moreover, for the patient to interpose a respiration pause up to a maximum length of double the expiration time or to slow down the frequency with respect to the fixed value for a limited time. If the patient becomes unconscious during the assisted respiration, the respirator immediately transfers to a reduced respiration and at the latest after six respiration cycles transfers back to completely controlled respiration.

The control signal for the inspiration consists, as in the controlled respiration, of a pressure signal beginning at the value of the preceding final expiratory pressure. In the case of a control by the patient, there is, however, no delay permissible since the patient immediately requires assistance with his inspiration.

The transition from pressure to flow regulation is effected according to the same criteria as in the controlled respiration.

When the patient is conscious, it is conceivable that he desires more flow than the logic makes available to him with its decreasing flow ramp. Because the patient acts against this flow regulation, the mouth pressure sinks in this phase and the value of the fixed final expiratory pressure can already be attained in phase II. This fact is utilized in the present regulation in order to allow the patient to inspire more air. As soon as this event occurs, the regulator again switches to pressure regulation. In so doing, the constant final expiratory pressure remains in existence until the beginning of a new respiration cycle.

If phase II has not been interrupted by the aforementioned pressure regulation, the expiratory phase III proceeds as in the controlled respiration. However, to avoid air-trapping, control by the patient during this phase is blocked.

In order not to cause false triggering, during expiration the pressure signal is never allowed to become smaller than the fixed final expiratory pressure. If, therefore, in assisted operation the pressure of the inflexion is chosen smaller than the final expiratory pressure, then the inflexion is brought to the level of the fixed final expiratory pressure by the logic. The transition from phase III to phase IV is effected as in the controlled respiration. During phase IV, the patient can control a new inspiration. For the control by the patient there is a question of the following criterion: reversal of the flow direction with a certain amplitude and a certain duration. As is shown in the following, this criterion must differentiate from coughing; therefore, a relatively complex criterion has been chosen for the control.

Figure 4:
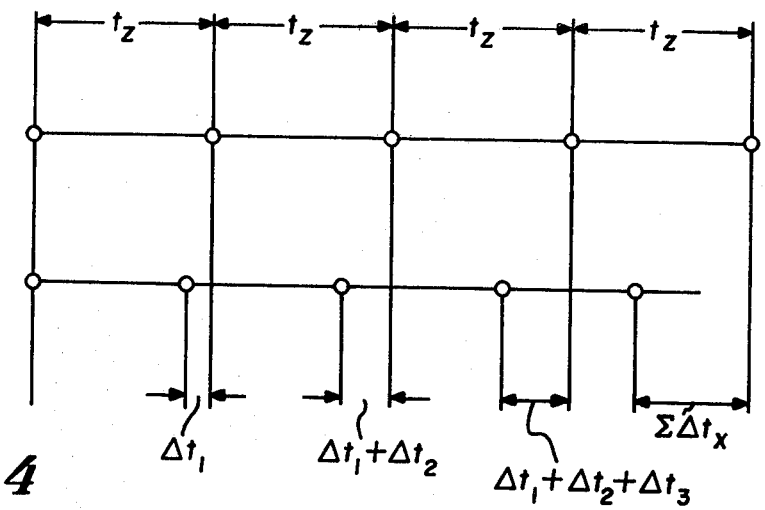
FIGS. 4 and 5 graphically illustrate suitable possibilities of respiration freedom on the part of the patient in the assisted respiration mode of operation of the respirator.
Figure 5:
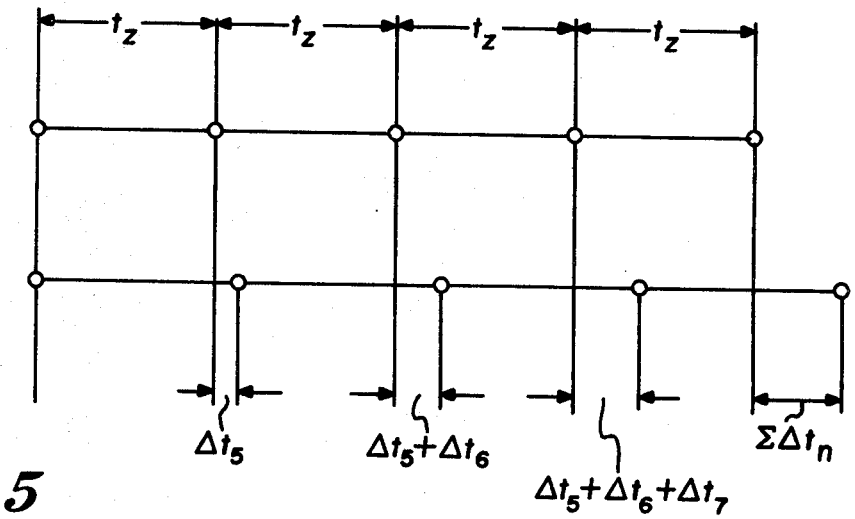

A respiration pause is made possible as follows: By the possible patient control, the precalculated duration of expiration (phases III and IV) can be reduced or, as is shown in the following, also be increased. The time difference resulting from a switching to a respiration pause is continuously summed until a stored value of a maximum expiration duration is attained. Then, a new cycle is initiated without control by the patient. In FIGS. 4 and 5, suitable possibilities of respiration freedom are shown by way of examples. FIG. 4 shows the control by the patient before completion of the cycle time required by the fixed frequency. The upper line shows the normal cycle completion, while the lower line represents the cycle completion accelerated by control of the patient. Under this is given the time reserve resulting by the control by the patient with respect to the normal cycle. The time reserves $\Delta t$ resulting from the control established by the patient are continuously stored by the logic and summed up to a maximum value $\Sigma \Delta t_x$ e.g. in the magnitude of the calculated expiration time $t_2$, and retained in storage.

Thus resulting time reserves now also give the patient the possibility of switching to respiration pauses. This possibility is shown in FIG. 5, in which the upper line again represents the normal cycle completion, while the lower line again gives the cycle completion delayed by respiration pauses. Below the lower line are given the time reserves utilized by the respiration pauses. The patient can switch to respiration pauses until the time reserves $\Sigma \Delta t_x$ emanating from the control by the patient is used up, i.e.

$$\Sigma \Delta t_x = \Sigma \Delta t_n$$

After exhaustion of this time reserve $\Sigma \Delta t_x$, it is no longer possible for the patient to extend the respiration cycle time above the calculated value $t_z$.

This example shows that the average respiration frequency either remains constant if the speeding up resulting from control by the patient and the respiration pauses constantly balance one another, or increases if the sum of the times from the speeding up exceed the value of $t_2$ (expiration time) before respiration pauses are effected.

In this manner, it is possible to maintain in a simple way the fixed minimal minute volume. For this, the same logic is utilized as for the controlled respiration, i.e. by calculating an inspiratory nominal volume which not only takes account of the fixed magnitude but also of the volume actually expired (feedback of the six respiration cycles).

The feedback after six respiration cycles takes on a new significance in spontaneous respiration. If the patient desires more air, i.e. a greater minute volume than that fixed by the apparatus, then the calculated inspiratory nominal volume is reduced in the next six respiration cycles and the patient thereby receives somewhat more freedom, at least as long as he breathes sufficiently spontaneously. By the choice of the minute volume in the assisted respiration, the intensity of the respiration assistance can accordingly be adjusted. In the extreme case, the fixed minute volume is an absolute minimal value which cannot be subordinated.

It is of great importance that in the case of coughing by the patient, the regulation has the correct response. With coughing, the patient must be calmed in order that the normal respiration course can be guaranteed as quickly as possible. In so doing, the previously described functioning of the regulator must not be impaired (such as, for example, the feedback of the six respiration cycles). Further, the logic must be able to differentiate an inspiration control by the patient from a cough signal. For this purpose, the criterion for coughing shown in FIG. 7 has been determined. According to this, the regulation ascertains a cough when the following criteria are fulfilled:

a. The gradient of the flow must exceed a certain magnitude,
 b. the flow must have the opposite sign to normal, i.e. during phases I and II (inspiration) it must have the sign of expiration and during phases III and IV (expiration) it must have the sign of inspiration.

The time in which the conditions a and b are simultaneously fulfilled plus a calming time $\Delta t$ is defined as the cough duration.

Figure 6:
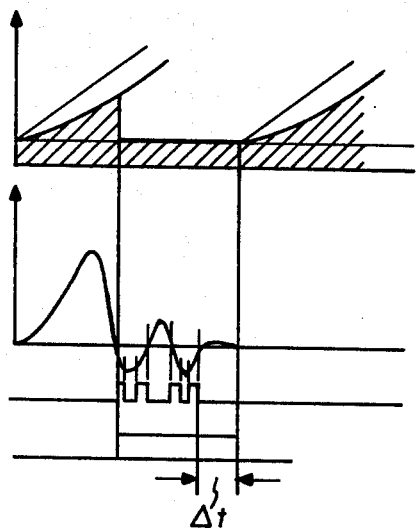
FIGS. 6 and 7 graphically represent the determination of the criteria for a coughing condition, occurring respectively during the inspiratory and expiratory portions of a breathing cycle.
Figure 7:
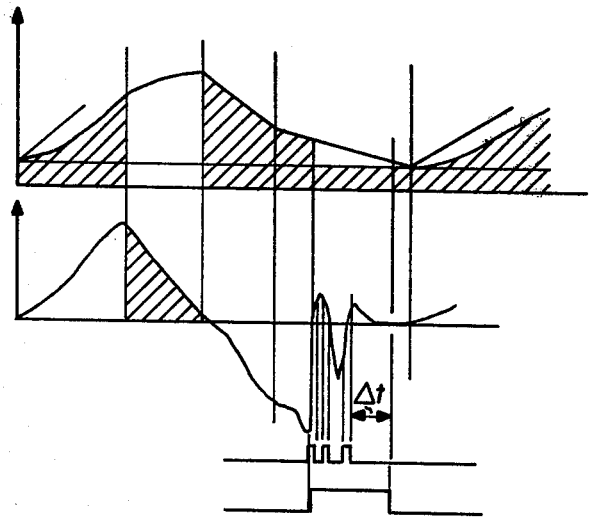

During the entire cough duration, the respirator is switched to a regulation of the final expiratory pressure. Accordingly, the cough is not hindered and the patient can calm himself. If the patient coughs as indicated in FIG. 6, during inspiration, then after the cough duration, a new inspiration is started. If the patient coughs as shown in FIG. 7 during expiration, then the respirator remains at the final expiratory pressure until the end of the expiration time.

The cough logic only functions during the "controlled" and "assisted" methods of operation.

Figure 8:
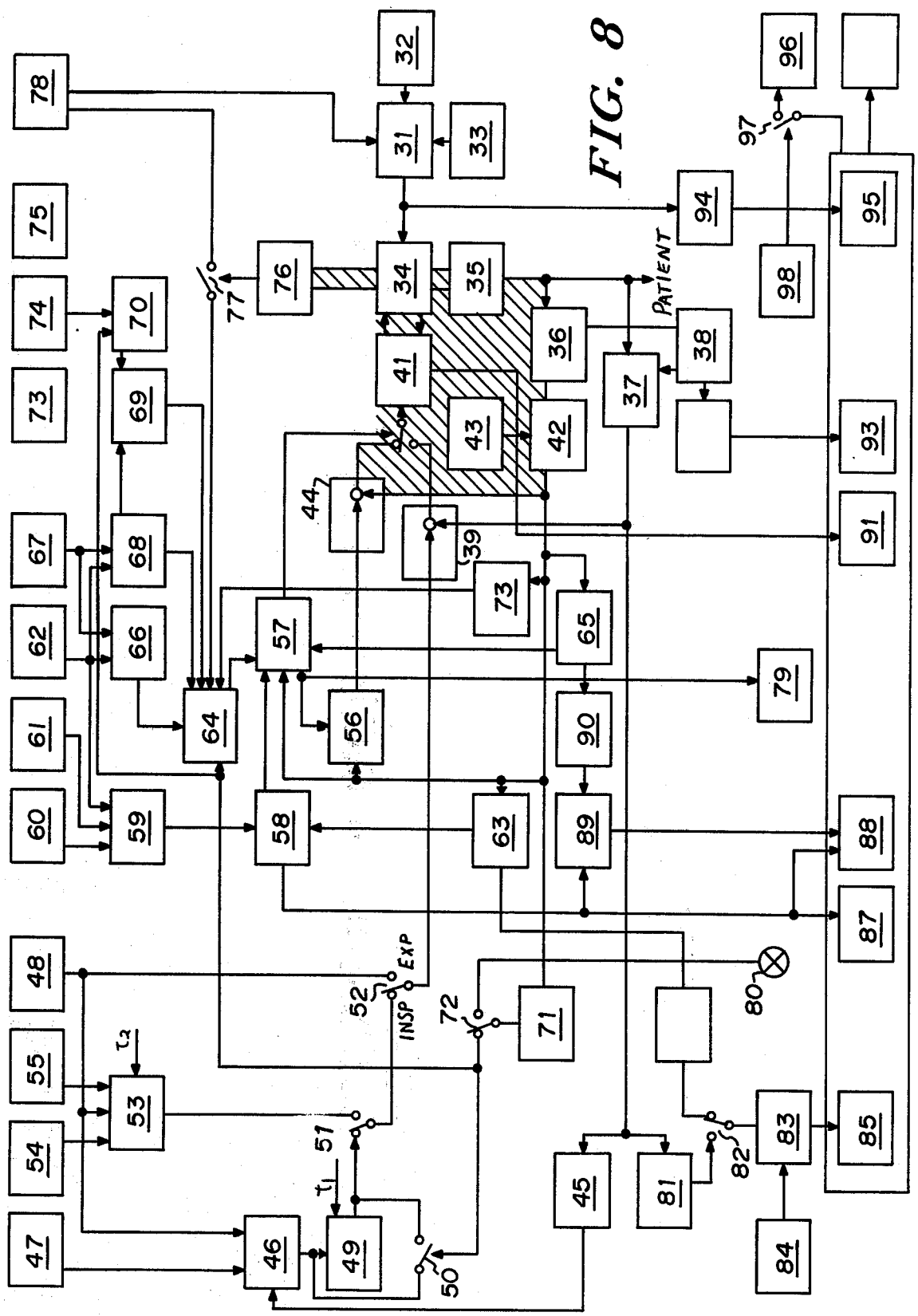
FIG. 8 is a schematic block diagram of an embodiment of a regulator in accordance with the invention.

The block diagram shown in FIG. 8 represents in the usual simplification, an example of regulator with which the previously described functions can be carried out. The device shown in FIG. 1 collectively as the respiration gas source 2 consists in the present example of a pump 31 which is provided with a mixing valve 32 and a unit 33 for the air humidification and temperature regulation. The valve 4 consists in the present case of a control valve 34 driven by a servomotor and a separate valve 35 for separating the expiration air from the inspiration air, which is denoted briefly and I/E valve.

The measuring device 5 shown in FIG. 1 consists, as already mentioned in the present embodiment, of a flow measuring apparatus 36 and a pressure measuring apparatus 37 separated therefrom. Sine in the present embodiment, the flow and pressure measurement is undertaken with the aid of an auxiliary flow, an auxiliary flow source 38 is provided which delivers the necessary auxiliary flow to the flow measuring device 36 and the pressure measuring device 37. The output signal of the pressure measuring apparatus 37 is delivered to a comparator circuit 39 for comparing the actual pressure value measured with a nominal value. The output signal of this comparator circuit 39 is delivered via a switch 40 to a circuit 41 for regulating the position of the servomotor indicating the control valve 34. In the same manner, the output signal of the flow measuring apparatus 36 representing the actual value measured is delivered via a compensation circuit 42 to a further comparator circuit 44 for comparing this actual valve with a nominal value for the flow. The output signal of the comparator circuit 44 is led via the switch 40 to the position regulator 41. The switch 40 accordingly serves for switching between flow and pressure regulation.

The compensation circuit 42 is necessary because the measured value of the flow depends on the composition of the respiration gas, and serves in order to compensate for this dependence. For this purpose, it receives a signal from a circuit 43 for detecting the composition of the gas mixture. The position at which the gas mixture is detected is optional, therefore no corresponding connection is drawn in. It can be expediently effected, however, at the mixing valve 32.

AT the output of the pressure measuring apparatus 37 is further connected a measuring circuit 45 in which a signal specifying the final expiratory pressure is determined for each respiration cycle from the output signal of the pressure measuring apparatus 37. The output signal of the circuit 45 is delivered to an input of a ramp generator 46. The ramp generator 46 has two further inputs, one of which is connected to the external control element 47 for selecting the ramp gradient of the inspiratory pressure $(dp/dt)_I$ and the second of which is connected to the external control element 48 for adjusting the final expiratory pressure. The ramp generator 46 produces a linearly increasing signal determining the pressure increase in phase I. In controlled respiration, this signal is delivered to a delay unit of the first order 49. This delay unit, as already mentioned in the previous function description, serves in order to ensure a smooth onset of the pressure increase. The delay unit 49 has a by-pass line via a switch 50, which in assisted respiration is connected in case of control by the patient during expiration.

The output signal of the delay circuit 49 or, in case of a control by the patient in assisted respiration, the output signal of the ramp generator 46 directly, serves as the nominal signal for the inspiratory pressure increase. During phase I of the inspiration, this signal is delivered via a switch 51 (for switching between inspiration and expiration) present in the switching position "inspiration" and a second switch 52 (for switching between on the one hand controlled or assisted respiration and on the other hand spontaneous respiration or disorders such as coughing etc.) present in the switching position "controlled/assisted" to the comparator circuit 39 where the comparison with the actual signal is effected.

During expiration, the switch 51 is present in its other switching position "expiration". In this phase of the respiration cycle, the pressure course is determined by a pressure function generator 53 which calculates the pressure function from the expiratory pressure decrease, the pressure of the inflexion and the final expiratory pressure. For this purpose, the pressure function generator 53 is connected on the input side with the external control element 54 for selecting the expiratory pressure decrease to the inflexion, the control element 48 for selecting the final expiratory pressure and the control element 55 for selecting the pressure of the inflexion. In the spontaneous respiration operating state or with disorders such as coughing, extended expiration time etc. the final expiratory pressure is simply specified as the nominal value. For this purpose, the switch 52 is present in its second switching position, i.e. the switching position which connects the external control element 48 directly with the comparator circuit 39.

From a flow function generator 56, the comparator circuit 44 receives the nominal value to be compared with the actual value of the flow measured. This function generator 56 determines the flow course in phase II of the inspiration from the instantaneous flow at the switching point between pressure and flow control the flow O at the end of the inspiration. For this purpose, the function generator 56 receives via one input the actual signal of the flow measured and via a second input the signal for switching from a logic circuit 57.

The flow function generator 56 is so designed in the present embodiment that the flow course decreases linearly from the instantaneous flow $V_x$ to the value 0. It is possible without more ado, however, to choose a flow course varying from a linear course, for example, an exponential.

The logic circuit 57 determines the switching from pressure to flow control during inspiration. For this purpose, it continuously calculates the residual volume already defined earlier, i.e. the difference between the nominal volume per respiration cycle and the volume inspired at the instant $t_x$, and the volume which is produced starting from the instantaneous flow at the instant $t_x$ to the flow 0 on the basis of the provided flow-course curve during phase II of the inspiration, and compares these two volumes with one another. In other words, the circuit 57 calculates the expression $$\dot{V} = \frac{(V_{act} - V_x) \, 2}{t_1 - t_x}$$

When this equation is fulfilled, the circuit 57 produces a signal for switching from pressure to flow control. For calculating this expression, four input signals are delivered to the circuit 57. Via one input, it receives the actual value of the flow measured from the flow measuring apparatus 36 via the compensation circuit 42. A second input is connected with a circuit 58 from which it receives a signal specifying the inspiratory nominal volume per respiration cycle.

The circuit 58 serves for comparing the buccal nominal volume per respiration cycle which is specified on the basis of the value given by the doctor, with the expired volume per respiration cycle averaged over six respiration cycles and corrects the nominal volume if the two compared values deviate from one another. The circuit 58 receives the value of the inspiratory nominal volume per respiration cycle from a circuit 59, in which this volume is calculated from the minute volume and the respiration frequency. In the present embodiment, the circuit 59 has for this purpose three inputs, the first of which is connected with the external control element 60 for selecting the alveolar minute volume, the second of which is connected with the external control element 61 for adjusting the dead volume and the third of which is connected with the external control element 62 for adjusting the respiration frequency. The circuit 58 receives the value of the expired volume per respiration cycle averaged over six respiration cycles, from a circuit 63 in which this value is calculated from the actual value of the flow measured during the expiration.

Via a further input, the circuit 57 receives the time signal $t_x$ from a timer logic 64 in which this time signal is calculated for controlled respiration essentially from the fixed values for the temporal sequence of the respiration cycle; with consideration of further criteria for assisted respiration.

Finally, the circuit 57 receives a signal specifying the instantaneous volume during inspiration from a circuit 65, in which this inspiratory instantaneous volume is continuously calculated from the actual value of the flow measured. For this purpose, the circuit 65 is also connected to the output of the compensation circuit 42 and therewith, to the flow measuring apparatus 36.

In the case of controlled respiration, the timer 64 utilizes the inspiration time $t_1$ and the expiration time $t_2$ for determining the temporal sequence of the respiration. The inspiration time $t_1$ is calculated in a circuit 66 from the respiration frequency and the ratio of inspiration to expiration. For this purpose, the circuit 66 has two inputs, one of which is connected with the external control element 62 for selecting the respiration frequency and the second of which is connected with an external control element 67 for selecting the ratio of inspiration to expiration. In the same manner, the expiration time $t_2$ is calculated in a circuit 68 which likewise has one input each connected with the control elements 62 and 67.

In the case of assisted respiration, the timer circuit 64 additionally takes into account a series of time factors, One of these time factors is the extended expiration time $t_2'$, which is calculated in a circuit 69. For this calculation, there is called upon the expiration time $t_2$ determined by the circuit 68 and the time reserve with respect to the normal cycle summed in an addition circuit 70. This time reserve, i.e. the sum of the separate differences between the specified cycle times and the cycles shortened by the spontaneous control by the patient, is calculated in the circuit 70 on the basis of a signal which it receives from a logic circuit 71, which furnishes a corresponding signal in the case of control by the patient on the basis of certain criteria of the flow course. This signal can of course only be delivered to the circuit 70 in the "assisted" switching position of a switch 72. The input of the logic circuit 71 is connected with the flow measuring apparatus 36 via the compensation circuit 42. Utilized as a criterion for this is, as already mentioned, that a control by the patient effects the reversal of the flow direction with a certain amplitude and a certain duration.

The signal indicating the instant of control by the patient is also delivered directly to the timer circuit 64 as a further input value for the assisted respiration.

A third, additional input value for the assisted respiration is the output signal of a logic circuit 73 which indicates the presence of a cough on the basis of certain criteria of the flow course and can by this means be denoted as the cough logic. The cough logic 73 is connected on the input side with the flow measuring apparatus 36 again via the compensation circuit. A flow with a sign opposite to normal and a gradient lying above a certain limiting value is admitted as the criterion for the occurrence of a cough as opposed to the occurrence of a control by the patient.

Apart from the said control elements for selecting the input values, there are also the control elements for selecting the operating condition, i.e. a control element 73 for engagement of controlled respiration, a control element 74 for engagement of assisted respiration and a control element 75 for engagement of spontaneous respiration. These three control elements are expediently combined in a single selection switch. Its connection to the individual elements of the regulator is half not shown in the block diagram for clarity. For the person skilled in the art, it is evident without more ado how the operating selection is to be undertaken.

A device 76 for the manual modulation of the control valve 34 is provided for the "hand control" operating condition.

Finally, a control element 78 is provided for engagement of the whole regulator and the pump 31.

As already mentioned, the regulation has a series of indicator and alarm devices. One indicator serves for visually representing the temporal ratios of pressure and flow regulation, i.e. the phases I and II. This indication can be undertaken, for example, with a number of linearly arranged lamps, whose total number corresponds to the inspiration time and one section of which lights up corresponding to phase II, while the other remains switched off. Obviously another type of indication would be possible, for example, on an analogue instrument.

The switch 72, which in assisted respiration connects the logic circuit 71 with the pressure control loop, is in its second switching position in controlled respiration and connects the output of the logic circuit 71 with an indicator 80 by which means the control pulses accordingly released with controlled respiration by the patient are indicated. The occurrence of such control pulses in controlled respiration, signifies that the patient is opposing the respirator. The indicator 80 gives an indication by these, then, that the controlled respiration has possibly to be replaced by an assisted respiration. The indicator 80 can consist, for example, of a lamp. An additional acoustic signalling is not necessary, because the occurrence of these control pulses is not critical.

For a series of further magnitudes, however, there is provided a continuous monitoring and an alarm production with excession of fixed limiting values. The regulation automatically provides for the maintenance of the most important parameters fixed by the doctor. This automatic accommodation of the patient is effected in a certain working range. Only when this accommodation is no longer possible, is an alarm triggered and the disorder causing the alarm simultaneously indicated. Besides this, magnitudes are also monitored which are not externally adjustable. These free magnitudes are dependent on the operating method. They are indicated via an analogous measuring instrument on which the alarm level can be simultaneously adjusted.

In this manner, the final respiratory pressure is monitored in the controlled and the assisted respiration. For this purpose, the signal coming from the pressure measuring apparatus 37 is delivered to a measuring device 81 in which the final inspiratory pressure is retained for each inspiration. The output signal of this measuring device is delivered to an analogue measuring instrument 83 via a switch 82 present in the controlled/assisted switching position. The measured value for the final inspiratory pressure is indicated on this instrument. An alarm limiting value can be simultaneously adjusted with the aid of an adjustment device 84. With excession of this alarm limiting value, an alarm is given out by an alarm device 85 connected with the analogue measuring instrument. This alarm can be visual and/or acoustic, in which for the acoustic alarm an optionally introduced delay of up to 1 minute can be expediently provided.

The final inspiratory pressure is measured since it is of an unspecified magnitude. Its measurement takes the place of the usual measurement of average respiration pressure. All other pressure values during a respiration cycle are determined, in that the pressure course in phases I, III and IV is fixed by the doctor.

When switch 52 is present in its second switching position "spontaneous" and switch 40 is present in its lower switching position, a pressure regulation takes place in which the final expiratory pressure continuously made available to the patient is excluded, while the function of a device for monitoring the respiration minute volume carries out the remaining part. The expiratory volume per cycle calculated in circuit 63 and averaged over six respiration cycles is converted to the minute volume in a computing circuit 86. This minute volume is indicated in the analogue measuring instrument 83, an alarm device 85 again being controlled when exceeding a specific limiting value adjusted with the aid of the adjustment device 84. The comparator circuit 58, in which the nominal volume per cycle is compared with the expired volume per cycle averaged over six cycles, produces a signal with a difference exceeding 20% with which an alarm device 87 is controlled. Consequently, the alarm device 87 indicates a leak in the system when the expired volume is more than 20% below the inspired volume per respiration cycle.

A further alarm device 88 is controlled when the respiration paths of the patient are congested, i.e. when a mouth cleansing is necessary or when an incorrect pressure increase is fixed for the patient. This alarm is triggered when simultaneously the difference signal from the circuit 58 is applied and the nominal volume is not attained at the end of inspiration. The second of these two criteria is obtained in the comparator circuit 89, which via one input receives a signal specifying the inspiratory nominal volume from the circuit 58 and via a second input receives a signal specifying the final inspiratory actual volume. This final inspiratory actual volume is calculated in a computing circuit 90, which is connected to the circuit 65. The inspired volume is continuously determined, as already explained earlier, in circuit 65. The two alarm devices 87 and 88 only come into function in controlled and assisted respiration.

Moreover, with all operating methods, there are monitored the function of the pressure pump or gas delivery, the function of the auxiliary flow source 38 and the function of the electronics. For the monitoring of the electronics, there serves an alarm device 91 which is connected, for example, with the position regulator 41. For the monitoring of the regulating function of the auxiliary flow source 38, there serves a measuring apparatus 92 with which an alarm device 93 is connected. Finally, for the monitoring of the pump, a pressure measuring apparatus 94 is provided, to which an alarm device 95 is connected. If an external gas source is provided instead of the pump 31, the pressure measuring apparatus 94 can of course be connected into the line coming from this gas source.

In the present embodiment, each alarm device is visual, i.e. it consists of an indicator lamp. An acoustic alarm device 96 is additionally provided, which produces an acoustic signal for each state of alarm. The localizing of the disorder can then be effected on the basis of the visual signal. If desired, the acoustic alarm can be delayed by up to 1 minute with the aid of a switch 97 and a timer 98. A continuous blocking of the alarm is not provided.

In the present embodiment of the regulator, the following possibilities for adjustment of the control elements are provided:

The adjustment of the inspiratory pressure increase can be fixed stepwise from a value of 10 cm $H_2O$/second, in 10 steps each of 10 cm $H_2O$/second, up to 100 cm $H_2O$/second. For indicating phases I and II with a series of lamps, there are taken, for example, 16 lamps.

The pressure decrease during phase III of the expiration is adjustable in 10 steps, as follows:

500; 250; 100; 80, 60; 50, 40; 30; 20; 10 cm $H_2O$/sec

The pressure level of the inflexion is adjustable in 9 steps:

−20; −15; −10; −5; 0; 5; 10; 15; 20 cm $H_2O$

The final expiratory pressure is adjustable in 9 steps as follows:

−10; −7.5; −5; −2.5; 0; 2.5; 5; 7.5; 10 cm $H_2O$

The respiration frequency should have the range from 8 to 60 respiration cycles per minute. For practical reasons, however, in the present embodiment the range from 2 to 58 has been chosen, that is with adjustment steps of 2 respiration cycles per minute.

The ratio of inspiration to expiration is adjustable between 1/1 and 1/3 in 9 steps, as follows:

1/1; 1/1.25; 1/15; 1/1.75; 1/2; 1/2.25; 1/2.5; 1/2.75 1/3

Since in the present embodiment, instead of the buccal respiration minute volume, there can be chosen separately the alveolar respiration minute volume and the dead volume, with frequency variation with the alveolar ventilation remains automatically constant. The alveolar respiration minute volume can be selected in 50 steps between 0.5 and 10 liters per minute. For practical reasons, the following subdivision has been chosen here:

0.6; 0.8; 1.0; 1.2; 1.4; ... 9.8 liters per minute

For the adjustment of the dead volume, the following 25 steps are available:

0.00; 0.02; 0.04; 0.6; 0.08; 0.10; ... 0.48 liter

If the dead volume is adjusted to 0.00 liter, then the fixed alveolar respiration minute volume corresponds to the buccal respiration minute volume.

The adjustment steps can, of course, be chosen otherwise. In certain cases, e.g. for the respiration of children, a greater resolution than that specified is necessary for some values.

Instead of the digital adjustment, a stepless analogue adjustment for a number or for all of the values could also be chosen.

What is claimed is:

1. Regulation of the flow and pressure of the respiration gas in a respirator during the respiration cycle in which the actual flow and pressure of the respiration gas are measured via a measuring device arranged proximate the patient connection and the measured values thereof are converted into electrical signals and in which the flow and pressure of the respiration gas are controlled during the inspiration and expiration portions of the respiration cycle via valve means arranged between the respiration gas source and the measuring device, comprising:

measuring the actual flow of respiration gas proximate the patient;

measuring the actual pressure of respiration gas proximate the patient, calculating nominal values of flow and pressure from preselected fixed values and said actual values;

comparing the actual values measured for the flow and pressure with said nominal values; and obtaining from said comparison a control signal for modulating the valve means and thereby regulating the flow and pressure of the respiration gas wherein the inspiration portion of the respiration cycle is comprised of two phases, and wherein said regulation includes pressure-regulating the first of said two phases and flow-regulating the second of said two phases.

2. Regulation according to claim 1 including effecting changeover from said first to said second inspiration phase at the point in which the difference between the inspiratory nominal volume and the instantaneous volume is equal to the volume which is calculated from the instantaneous flow and a flow decreasing to 0 from that point to the end of the inspiration phase.

3. Regulation according to claim 2 including comparing the inspiratory nominal volume with a value of the expired volume averaged over a predetermined number $x$ of respiration cycles and correcting the nominal volume correspondingly for $x$ subsequent respiration cycles.

4. Regulation according to claim 3 including triggering alarm means upon a difference occurring between the inspiratory nominal volume per respiration cycle and the average value lying above a pre-established limiting value.

5. Regulation according to claim 4 including producing when the difference between the nominal volume per respiration cycle and the average value and the difference between the final inspiratory actual volume and the nominal volume each simultaneously exceed a predetermined limiting value.

6. Regulation according to claim 2 including directing the flow of respiration gas from the instantaneous value at the changeover points to 0 according to a predetermined function.

7. Regulation according to claim 6 wherein said predetermined function is a straight line.

8. Regulation according to claim 2 including measuring the instantaneously inspired volume continuously from the flow measured.

9. Regulation according to claim 1 including altering the regulator, with a flow measured having the sign of expiration during the inspiratory portion of the respiration cycle or vice-versa and a gradient lying above a predetermined limiting value which characterize a cough criterion, to provide a fixed final expiratory pressure.

10. Regulation according to claim 9 wherein upon the occurrence of a flow characterizing the cough criterion during an inspiration, a new inspiration is begun following a pause of predetermined duration, and wherein upon the occurrence of a flow characterizing the cough criterion during an expiration, the final expiratory pressure is interposed and the end of the respiration cycle awaited.

11. Regulation according to claim 1 wherein upon a reversal of the flow direction of a predetermined amplitude and duration during the expiration time, the inspiration portion of the subsequent respiration cycle is immediately interposed.

12. Regulation according to claim 11 wherein the time difference between the preestablished cycle duration provided and the cycle duration shortened by respiration control effected by the patient is stored and summed over a plurality of respiration cycles.

13. Regulation according to claim 12 wherein the summed time reserve can be utilized in later respiration cycles in the sense of a cycle extension.

14. Regulation according to claim 1 wherein the pressure course during the first phase of inspiration follows a curve which proceeds from the measured final expiratory pressure of the preceding respiration cycle and has an externally selected gradient.

15. Regulation according to claim 14 including providing the pressure course curve with a delayed insert.

16. Regulation according to claim 14 including starting the pressure-course curve without a delay in the case of a respiration control being provided by the patient.

17. Regulation according to claim 1 wherein the pressure-course during expiration is comprised of two phases.

18. Regulation according to claim 17 wherein the pressure-course in the first phase of expiration decreases linearly to a preestablished pressure with a predetermined gradient.

19. Regulation according to claim 18 wherein the pressure-course in the second phase of expiration proceeds from the specified pressure and ends at a preestablished fixed final expiratory pressure.

20. Regulation according to claim 19 wherein in an assisted respiration mode of operation, no pressure lying below the value of the final expiratory pressure is allowed.

21. Regulation according to claim 17 wherein a fixed limiting value is preestablished for the temporal ratio of the two phases.

22. Regulation according to claim 1 wherein the final inspiratory pressure is measured and displayed.

23. Regulation according to claim 1 wherein the expired minute volume is calculated and displayed.

24. Regulation according to claim 1 wherein the temporal ratio of pressure to volume control during inspiration is displayed.

* * * * *

UNITED STATES PATENT OFFICE
CERTIFICATE OF CORRECTION

PATENT NO. : 3,961,627
DATED : June 8, 1976
INVENTOR(S) : HEINI ERNST ET AL

It is certified that error appears in the above-identified patent and that said Letters Patent are hereby corrected as shown below:

Column 16, Claim 9, line 26 "regulator" should be

--regulation--.

Signed and Sealed this

Second Day of November 1976

[SEAL]

Attest:

RUTH C. MASON
Attesting Officer

C. MARSHALL DANN
Commissioner of Patents and Trademarks